US005558656A

United States Patent [19]
Bergman

[11] Patent Number: 5,558,656
[45] Date of Patent: Sep. 24, 1996

[54] SANITARY NAPKIN HAVING AN INTERNAL SHAPING COMPONENT

[75] Inventor: Carl L. Bergman, Loveland, Ohio

[73] Assignee: The Procter & Gamble Company, Cincinnati, Ohio

[21] Appl. No.: 225,411

[22] Filed: Apr. 8, 1994

Related U.S. Application Data

[63] Continuation-in-part of Ser. No. 170,487, Dec. 20, 1993.
[51] Int. Cl.$^6$ ........................................................... A61F 13/15
[52] U.S. Cl. ........................ 604/385.1; 604/387; 604/378
[58] Field of Search ............................... 604/385.1–402, 604/378

[56]    References Cited

U.S. PATENT DOCUMENTS

| Re. 24,137 | 4/1956 | Jacks | 128/290 |
|---|---|---|---|
| 825,122 | 7/1906 | Greenwald . | |
| 2,331,355 | 10/1943 | Strongson . | |
| 2,747,575 | 5/1956 | Mercer | 128/290 |
| 2,964,039 | 12/1960 | Johnson, Jr. et al. | 128/290 |
| 3,183,909 | 5/1965 | Roehr | 128/290 |
| 3,343,543 | 9/1967 | Glassman | 128/290 |
| 3,575,174 | 4/1971 | Mogor | 128/290 |
| 3,654,929 | 4/1972 | Nilsson et al. | 128/287 |
| 3,865,112 | 2/1975 | Roeder | 128/290 R |
| 4,046,147 | 9/1977 | Berg | 128/290 R |
| 4,195,634 | 4/1980 | Disalvo et al. | 128/290 R |
| 4,217,901 | 8/1980 | Bradstreet et al. | 128/290 R |
| 4,340,058 | 7/1982 | Pierce et al. | 128/287 |
| 4,405,326 | 9/1983 | Lenaghan | 604/385 |
| 4,425,130 | 1/1984 | Desmarais | 604/389 |
| 4,430,086 | 2/1984 | Repke | 604/385 |
| 4,433,972 | 2/1984 | Malfitano | 604/385 |
| 4,446,189 | 5/1984 | Romanek | 428/152 |
| 4,490,147 | 12/1984 | Pierce et al. . | |
| 4,576,596 | 3/1986 | Jackson et al. | 604/370 |
| 4,585,448 | 4/1986 | Enloe | 604/378 |
| 4,595,392 | 6/1986 | Johnson et al. | 604/385 A |

(List continued on next page.)

FOREIGN PATENT DOCUMENTS

| 0102245A2 | 3/1984 | European Pat. Off. . |
|---|---|---|
| 0335252A2 | 3/1989 | European Pat. Off. . |
| 0426197A2 | 11/1990 | European Pat. Off. . |
| 0530781A2 | 3/1993 | European Pat. Off. . |
| 0572033A2 | 12/1993 | European Pat. Off. . |
| 0603497A1 | 6/1994 | European Pat. Off. . |
| 0604731A1 | 7/1994 | European Pat. Off. . |
| 2168612 | 6/1986 | United Kingdom . |
| WO91/03999 | 4/1991 | WIPO . |
| WO92/07535 | 5/1992 | WIPO . |
| WO92/10984 | 7/1992 | WIPO . |
| WO93/01785 | 2/1993 | WIPO . |
| WO93/01783 | 2/1993 | WIPO . |
| WO93/01782 | 2/1993 | WIPO . |
| WO93/01784 | 2/1993 | WIPO . |
| WO93/01781 | 2/1993 | WIPO . |
| WO93/12747 | 7/1993 | WIPO . |
| WO93/12746 | 7/1993 | WIPO . |
| WO93/21879 | 11/1993 | WIPO . |
| WO94/00292 | 1/1994 | WIPO . |
| WO94/05244 | 3/1994 | WIPO . |
| WO94/05243 | 3/1994 | WIPO . |
| WO94/16658 | 8/1994 | WIPO . |
| WO95/12488 | 5/1995 | WIPO . |

OTHER PUBLICATIONS

Translation of German Patent No. DE 3,517,192 A1.

Primary Examiner—John G. Weiss
Assistant Examiner—K. M. Reichie
Attorney, Agent, or Firm—Gerry S. Gressel; Larry L. Huston; E. Kelly Linman

[57]    ABSTRACT

A sanitary napkin is disclosed. The sanitary napkin has a liquid pervious topsheet, a liquid impervious backsheet, and an absorbent core disposed intermediate the topsheet and the backsheet. The sanitary napkin has a first Z-direction caliper at a Z-direction compressive load of 2 grams and a second Z-direction caliper at Z-direction compressive load of less than 100 grams, wherein the second Z-direction caliper is at least 15 millimeters less than the first Z-direction caliper.

10 Claims, 5 Drawing Sheets

5,558,656
Page 2

U.S. PATENT DOCUMENTS

| | | | |
|---|---|---|---|
| 4,614,679 | 9/1986 | Farrington, Jr. et al. | |
| 4,627,848 | 12/1986 | Lassen et al. | 604/370 |
| 4,631,062 | 12/1986 | Lassen et al. | 604/385 R |
| 4,654,040 | 3/1987 | Luceri | 604/385 R |
| 4,673,403 | 6/1987 | Lassen et al. | 604/385 R |
| 4,685,915 | 8/1987 | Hasse et al. | 604/378 |
| 4,758,240 | 7/1988 | Glassman | 604/379 |
| 4,790,838 | 12/1988 | Pigneul et al. | 604/366 |
| 4,804,380 | 2/1989 | Lassen et al. | 604/385.1 |
| 4,828,555 | 5/1989 | Hermansson | 606/379 |
| 4,883,707 | 11/1989 | Newkirk | 428/219 |
| 4,886,513 | 12/1989 | Mason, Jr. et al. | 604/385.1 |
| 4,892,536 | 1/1990 | Desmarais et al. | 604/385.2 |
| 4,904,249 | 2/1990 | Miller et al. | 604/378 |
| 4,911,701 | 3/1990 | Mavinkurve | 604/385.2 |
| 4,936,839 | 6/1990 | Molee et al. | 604/378 |
| 4,938,754 | 7/1990 | Mesek | 604/385.2 |
| 4,950,264 | 8/1990 | Osborn, III | 604/385.1 |
| 4,988,344 | 1/1991 | Reising et al. | 604/368 |
| 5,007,906 | 4/1991 | Osborn, III et al. | 604/385.1 |
| 5,057,096 | 10/1991 | Faglione | 604/385.1 |
| 5,092,860 | 3/1992 | Pigneul | 604/380 |
| 5,098,422 | 3/1992 | Davis et al. | 604/385.1 |
| 5,129,893 | 7/1992 | Thoren | 604/385.2 |
| 5,171,236 | 12/1992 | Dreier et al. | 604/369 |
| 5,171,302 | 12/1992 | Buell | 604/385.1 |
| 5,178,139 | 1/1993 | Angelillo et al. | 128/403 |
| 5,197,959 | 3/1993 | Buell | 604/385.1 |
| 5,211,641 | 5/1993 | Roos et al. | 604/385.1 |
| 5,290,262 | 3/1994 | Vukos et al. | 604/385.1 |
| 5,295,988 | 3/1994 | Muckenfuhs et al. | 604/385.2 |
| 5,300,054 | 4/1994 | Feist et al. | 604/378 |
| 5,300,055 | 4/1994 | Buell | 604/385.1 |
| 5,324,278 | 6/1994 | Visscher et al. | 604/385.1 |
| 5,342,337 | 8/1994 | Runeman et al. | 604/378 |
| B1 3,860,003 | 4/1989 | Buell | 604/385.2 |

5,558,656

SANITARY NAPKIN HAVING AN INTERNAL SHAPING COMPONENT

This is a continuation-in-part of application Ser. No. 08/170,487, filed on Dec. 20, 1993, and now abandoned.

FIELD OF THE INVENTION

The present invention relates generally to disposable absorbent articles such as sanitary napkins and, more particularly, to a sanitary napkin having an internal spring for displacing and shaping a portion of the sanitary napkin.

BACKGROUND OF THE INVENTION

Absorbent articles such as sanitary napkins, pantiliners, and incontinence pads are designed to absorb and retain liquid and other discharges from the human body, and to prevent soiling of the body and clothing by such discharges. It is generally desirable to provide absorbent articles such as sanitary napkins which maintain contact with the body of the wearer when they are worn, and which conform as closely as possible to the body of the wearer. Such body conforming capability is believed to increase the effectiveness of the sanitary napkin by reducing the possibility that menses will travel around the perimeter of the sanitary napkin and soil the wearer's body and/or clothing.

There have been a number of recent efforts to provide sanitary napkins and other absorbent articles with improved fit characteristics. Such recent efforts are described in U.S. Pat. No. 4,950,264 issued Aug. 21, 1990 to Osborn, U.S. Pat. No. 5,007,906 issued Apr. 16, 1991 to Osborn, U.S. Pat. No. 5,197,959 issued Mar. 30, 1993 to Buell, and U.S. patent application Ser. No. 07/605,583 entitled "Sanitary Napkin Having Components Capable of Separation In Use" filed Oct. 29, 1990.

While the sanitary napkins disclosed in these references represent advancements in the art, the search for new and different ways of improving body contact has continued.

It is especially desirable that the sanitary napkin maintain contact with and conform to the body of the wearer under dynamic conditions (when the wearer walks, sits, etc.). For instance, when the sanitary napkin is put on, the sanitary napkin is subjected to lateral compression by the upper portions of the wearer's thighs. The forces applied by the wearer's thighs generally tend to distort the shape of the sanitary napkin, reducing the size of the target the sanitary napkin provides.

One attempt to control the effect of these compressive forces is disclosed in UK Patent Application No. 2,168,612A, published Jun. 25, 1986. The UK patent application discloses a sanitary towel with a resilient insert positioned within the core or adjacent to a face of the core that is intended to inhibit permanent distortion of the towel. The UK application teaches that the insert resists lateral deformation of the sanitary towel, but does not teach or disclose a sanitary napkin having body conforming properties.

It is also desirable to provide a sanitary napkin which conforms to the wearer's body while maintaining the comfort of the wearer. Accordingly, a desirable sanitary napkin should maintain contact with the wearer's body, yet be capable of repeated elastic deflection to allow the wearer to comfortably assume different positions and to perform different activities.

Sanitary napkins are generally fastened to the wearer's undergarments by adhesive or other means. Movement of the wearer's undergarment relative to the wearer's body can result in the sanitary napkin shifting from the desired position. It is therefore also desirable to provide a body conforming sanitary napkin with a mechanism to accommodate independent movement between the body of the wearer and the wearer's undergarments.

It is therefore an object of this invention to provide an absorbent article, such as a sanitary napkin, which intercepts menses by conforming to the shape of the female urogenital region.

It is another object of the present invention to provide a sanitary napkin having a convexly shaped body facing surface.

It is yet another object of the present invention to provide a sanitary napkin having a spring for repeated elastic displacement of an absorbent core and a liquid pervious topsheet relative to a liquid impervious backsheet fastened to the wearer's undergarment.

A further object of the present invention is to provide a sanitary napkin having a non-absorbent internal spring disposed intermediate an absorbent core and a backsheet.

These and other objects of the present invention will be more readily apparent when considered in reference to the following description and when taken in conjunction with the accompanying drawings.

SUMMARY OF THE INVENTION

The present invention is an absorbent article, such as a sanitary napkin. The sanitary napkin of the present invention has a liquid pervious topsheet having a body facing surface, a liquid impervious backsheet joined to the topsheet, an absorbent core disposed intermediate the topsheet and the backsheet, and at least one nonabsorbent spring disposed intermediate the absorbent core and the backsheet. The spring provides Z-direction elastic displacement of a portion of the topsheet relative to the backsheet, and convexly shapes a portion of the body facing surface of the topsheet along a longitudinal centerline of the sanitary napkin.

The topsheet can be joined to the backsheet to provide independent movement of the topsheet and the absorbent core relative to the backsheet. In one embodiment the sanitary napkin has at least one longitudinally extending pleat joining the topsheet to the backsheet for controlling separation of the topsheet from the backsheet.

The spring can comprise a filament spring joined to the absorbent core at a first position coincident with the longitudinal centerline of the disposable absorbent article, and joined to the backsheet at laterally spaced apart positions symmetrically positioned with respect to the longitudinal centerline. The filament spring can have first and second legs arranged in an inverted V configuration as viewed along the longitudinal centerline of the sanitary napkin. In one embodiment the filament spring can comprise a plurality of closed loops symmetrically disposed with respect to the longitudinal centerline of the absorbent article.

The filament spring provides a sanitary napkin having a first Z-direction caliper at a Z-direction compressive load of about 2 grams, and a second Z-direction caliper at least 15 millimeters less than the first Z-direction caliper at a Z-direction compressive load of less than 100 grams. The filament spring can thereby promote body conformance and wearer comfort by maintaining the topsheet in contact with the wearer's body, while providing relatively low resistance to compression of the sanitary napkin in the Z-direction. The spring also provides a sanitary napkin having a lateral caliper of less than 10 millimeters at a lateral compressive load of 100 grams. The filament spring thereby permits the topsheet and core to be compressed laterally at relatively low lateral load levels to promote both wearer comfort and conformance of the topsheet and core with the wearer's body in the labial, perianal, and/or gluteal groove areas.

DETAILED DESCRIPTION OF THE INVENTION

Figure 1:
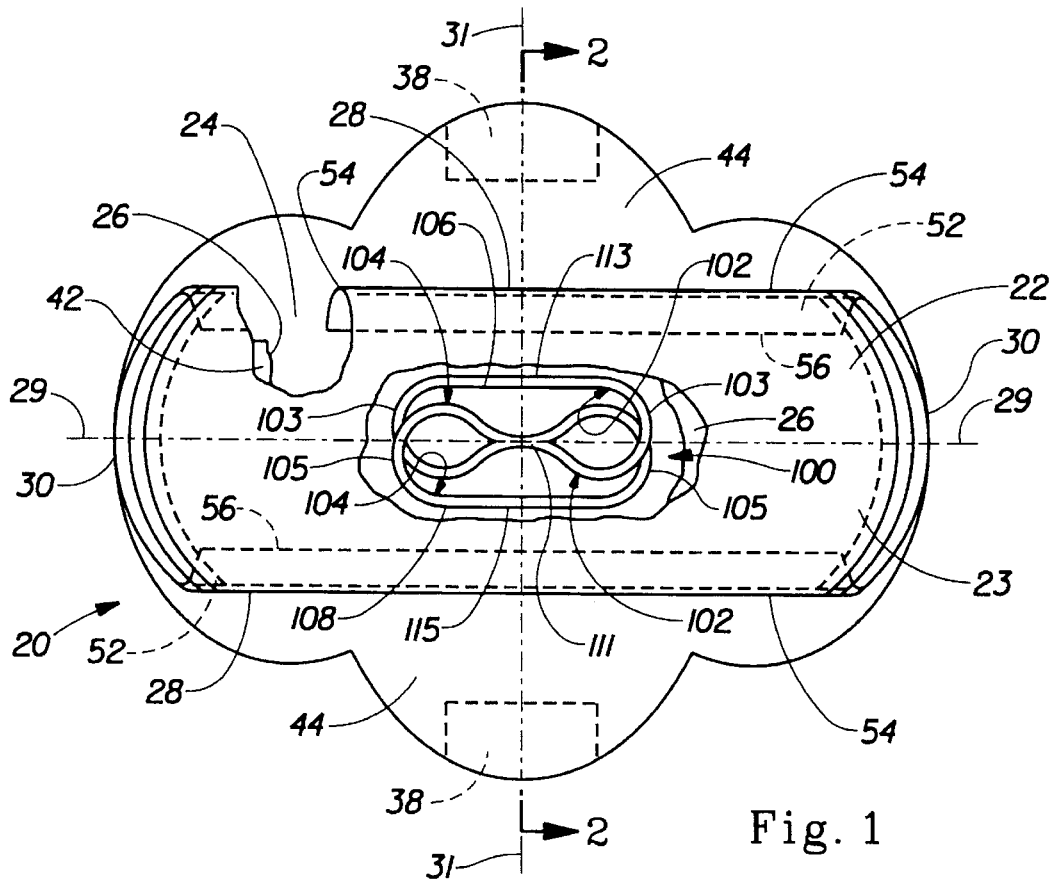
FIG. 1 is a top plan view of the sanitary napkin of the present invention with portions of the sanitary napkin shown cut away.
Figure 2:
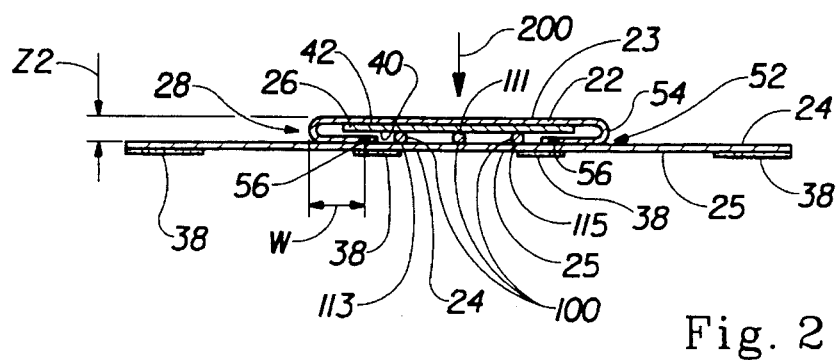
FIG. 2 is a section view taken along line 2—2 of FIG. 1 which shows the sanitary napkin of the present invention in a compressed configuration.
Figure 3:
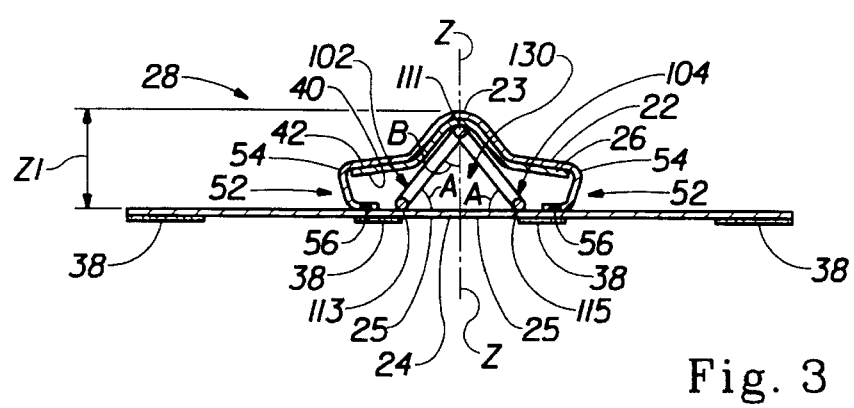
FIG. 3 is a section view of the sanitary napkin of FIG. 2 showing the sanitary napkin in an extended configuration.

FIGS. 1–3 illustrate a sanitary napkin 20 according to one embodiment of the disposable absorbent article of the present invention. As used herein, the term "absorbent article" refers to articles which absorb and contain body exudates. More specifically, the term is intended to include, but not be limited to, sanitary napkins, pantiliners, and incontinence pads (articles worn in the crotch region of a garment). The term "disposable" refers to articles which are intended to be discarded after a single use rather than laundered or otherwise restored or reused.

The sanitary napkin 20 comprises a liquid pervious topsheet 22 having a body facing surface 23, a liquid impervious backsheet 24 having a garment facing surface 25, an absorbent core 26 intermediate the topsheet 22 and the backsheet 24, and a spring 100 disposed intermediate the absorbent core 26 and the backsheet 24.

The sanitary napkin 20 has two longitudinal ends 28 and two lateral ends 30. The sanitary napkin also has a longitudinal centerline 29 and a lateral centerline 31. As used herein the term "longitudinal" refers to a line, axis, or direction generally aligned with the vertical plane which bisects the standing wearer into left and right body halves. The term "lateral" refers to a line, axis, or direction generally perpendicular to the longitudinal direction and lying in a plane generally parallel to the plane of the backsheet 24 when the sanitary napkin is supported in a generally flat configuration, as shown in FIGS. 1 and 2. The sanitary napkin 20 is typically longer in the longitudinal direction than in the lateral direction.

The "Z" direction refers to a line, axis, or direction which is perpendicular to the plane of the backsheet 24 when the sanitary napkin is supported in a generally flat configuration, as shown in FIGS. 1 and 2 (i.e., perpendicular to both the longitudinal axis 29 and the lateral axis 31 when the sanitary napkin is supported in a generally flat configuration). The Z-direction is illustrated in FIG. 3.

The spring 100 provides Z-direction elastic displacement of a portion of the topsheet 22 along the longitudinal centerline 29, and preferably a portion of the absorbent core 26, relative to the backsheet 24. The spring 100 also preferably convexly shapes a portion of the body facing surface 23 of the topsheet 22 along the longitudinal centerline 29, as shown in FIG. 3. The spring 100 thereby maintains contact of the topsheet 22 with the wearer's body, and shapes the top sheet 22 to conform to the wearer's body, particularly in the labial, perianal, or gluteal groove areas.

The spring 100 is disposed intermediate the backsheet 24 and the absorbent core 26 and preferably elastically displaces and shapes both the topsheet 22 and the core 26. At least a portion of the core 26 is thereby biased into contact with the topsheet 22 to receive body exudates passing through the liquid pervious topsheet 22. The spring 100 preferably extends between the core 26 and the backsheet 24 and preferably lifts the core 26 from the backsheet 24 to provide a void space 130. The void space 130 extends in the Z-direction from the backsheet 24 to the absorbent core 26. The void space 130 is desirable to ensure that the spring 100 is the only element providing resistance to displacement of the topsheet 22 and core 26 toward the backsheet 42, such as by a compressive load 200. Alternatively, the space between the backsheet 24 and the absorbent core 26 can be partially or completely filled with a material, such as an absorbent.

Figure 4:
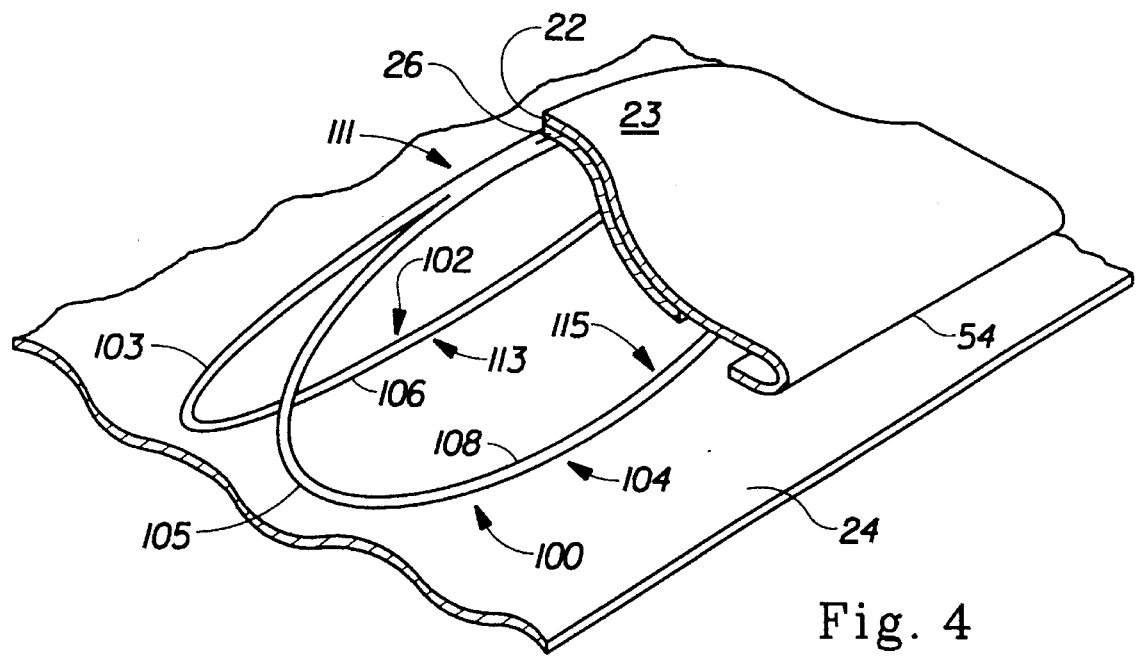
FIG. 4 is a partial perspective view of a sanitary napkin of the present invention in an extended configuration, with portions of the topsheet, absorbent core and backsheet cut away to show a filament spring comprising two closed loops disposed intermediate the absorbent core and the backsheet.
Figure 5:
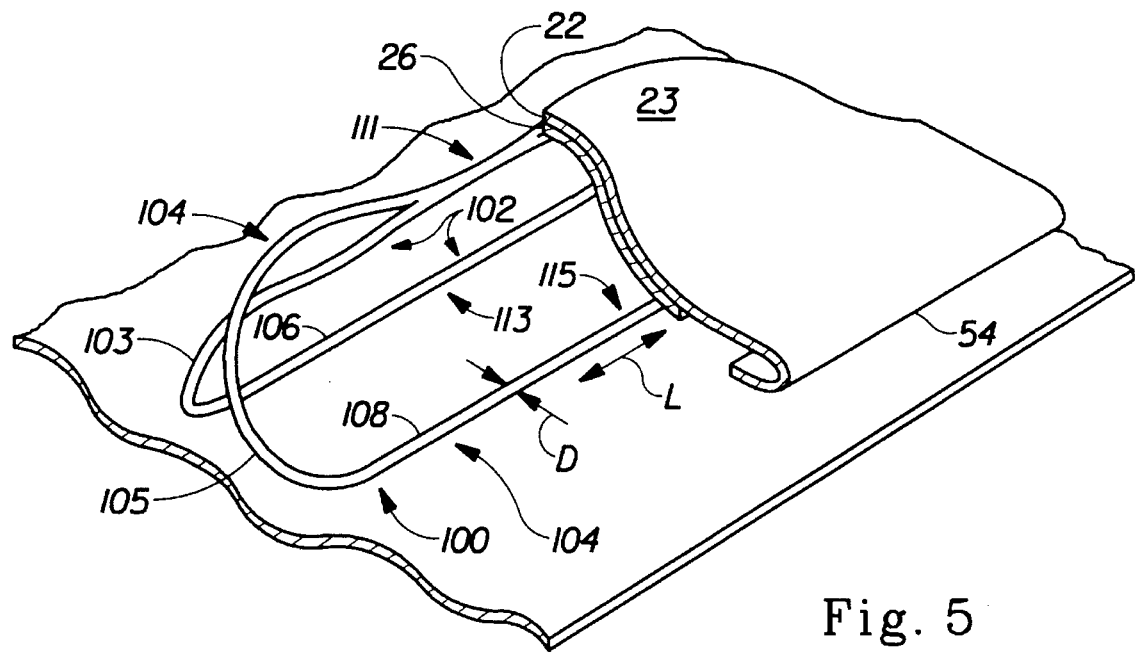
FIG. 5 is a partial perspective view similar to that of FIG. 4 showing a filament spring comprising closed loops overlapping in a scissors-like configuration.

By "Z-direction elastic displacement" of the topsheet 22 relative to the backsheet 24, it is meant that the topsheet 22 can be displaced relative to the backsheet 24 in the Z-direction from a first relatively unloaded, extended configuration having a Z-direction caliper Z1 shown in FIG. 3, to a second compressed configuration having a caliper Z2 shown in FIG. 2 (such as by a Z-direction compressive load 200 shown in FIG. 2), and that the spring 100 will restore the sanitary napkin 20 to have a Z-direction caliper which is at least about 70 percent of the Z-direction caliper Z1 upon removal of the compressive load when the sanitary napkin is dry and has not been loaded with body exudates. The elastic displacement of the topsheet 22 relative to the backsheet 24 can be expressed by the difference Z1–Z2. The procedure for measuring the dimensions Z2 and Z1 is described below. FIGS. 4 and 5 show the sanitary napkin in the relatively unloaded, extended position, with parts of the topsheet 22, core 26, and backsheet 24 cut away to show the spring 100.

The topsheet 22 and the backsheet 24 are joined together adjacent the longitudinal ends 28 and along one or both of the lateral ends 30. As used herein the term "join" refers to the condition where a first member or component is attached or connected to a second member or component either directly; or indirectly, where the first member or component is attached, or connected, to an intermediate member or component which in turn is attached, or connected to the second member or component.

Examining the components of the sanitary napkin 20 in more detail, the topsheet 22 is the component of the sanitary napkin 20 oriented towards and contacting the body of the wearer for receiving body exudates. The topsheet 22 is liquid pervious and should be flexible and non-irritating to the skin. As used herein the term flexible refers to materials which are compliant and readily conform to the shape of the body or respond by easily deforming in the presence of external forces. Preferably, the topsheet 22 is not noisy to provide discretion to the wearer. The topsheet 22 should be clean in appearance and somewhat opaque to hide the discharges collected in the core 26.

The topsheet 22 should exhibit good strike-through and rewet characteristics, permitting bodily discharges to rapidly penetrate the topsheet 22 to the core 26. A suitable topsheet 22 may be made from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet 22 comprises an apertured formed film. Suitable formed films are described in U.S. Pat. No. 3,929,135 issued Dec. 30, 1975 to Thompson; U.S. Pat. No. 4,324,246 issued Apr. 13, 1982 to Mullane et al.; U.S. Pat. No. 4,342,314 issued Aug. 3, 1982 to Radel et al.; U.S. Pat. No. 4,463,045 issued Jul. 31, 1984 to Ahr et al.; and U.S. Pat. No. 5,006,394 issued Apr. 9, 1991 to Baird; which patents are incorporated herein by reference. A preferred topsheet 22 comprises an apertured formed film joined to a nonwoven wipe acquisition sheet, as disclosed in U.S. Pat. No. 4,950,264 issued Aug. 21, 1990 to Osborn, which patent is incorporated herein by reference.

The backsheet 24 may be any flexible liquid impervious material, such as a polyolefinic film. The backsheet 24 prevents discharges collected by the sanitary napkin 20 from soiling the wearer or the wearer's clothing. The backsheet 24 can be a low density polyethylene film about 0.01 to about 0.05 millimeters in thickness. A suitable polyethylene film is sold by the Ethyl Corp., Visqueen Division, as Model XP-39385, and by the Clopay Corporation of Cincinnati, Ohio under the designation P18-1401.

The backsheet 24 can be larger than the topsheet 22 and the absorbent core 26, and preferably peripherally circumscribes the topsheet 22 and the core 26. The backsheet 24 may comprise flaps 44 extending outwardly from each longitudinal edge 28. The flaps 44 may be made in accordance with the teachings of U.S. Pat. Nos. 4,589,876 issued May 20, 1986 to Van Tilburg and 4,687,478 issued Aug. 18, 1987 to Van Tilburg, which patents are incorporated by reference. The backsheet 24 and the flaps 44 may be unitary and coextensive. Alternatively, the flaps 44 can be separate components joined to the backsheet 24.

The garment facing surface 25 of the backsheet 24 may comprise an attachment means 38 for securing the sanitary napkin 20 to the undergarment of the wearer. Preferred attachment means 38 include mechanical fasteners, or more preferably, pressure sensitive adhesive 38. The pressure sensitive adhesive 38 may be applied to the garment facing surface 25 in one or more strips or patches. As shown in FIGS. 1 and 2, the pressure sensitive adhesive can be disposed near the distal end of each flap 44, as well as on a portion of the backsheet 24 underlying the topsheet 22 and absorbent core 26. A suitable adhesive 38 is supplied as Century Adhesive A305-IV by the Century Adhesives Corp. of Columbus, Ohio.

The absorbent core 26 receives and contains body exudates, particularly menses. The core 26 should be flexible and nonirritating to the skin, and may have any number of shapes including a rectangular or hourglass shape. The core 26 has a first face 40 oriented towards the backsheet 24, and a second opposed face 42 oriented towards the topsheet 22.

Suitable materials from which the core 26 can be made include but are not limited to combinations of airfelt, such as cellulose wadding, and fibrated communition pulp; layers of tissue paper; and absorbent gelling materials. Examples of other suitable materials from which the core can be made include meltblown polymers; foams; chemically stiffened, modified or cross-linked cellulosic fibers; and synthetic fibers.

An exemplary core 26 comprises a laminate of tissue paper and absorbent gelling material. Such a core 26 is disclosed in U.S. Pat. No. 4,950,264 issued Aug. 21, 1990 to Osborn, and U.S. Pat. No. 5,007,906 issued Apr. 16, 1991 to Osborn et al., which patents are incorporated by reference for the purpose of teaching a suitable construction for the core 26.

The core 26 and the topsheet 22 are preferably joined together to form a laminate so that the core 26 and the topsheet 22 can be displaced by the spring 100 as a unit. The second face 42 of the core 26 can be joined to the topsheet 22 by any suitable means, with an adhesive attachment being preferred. A suitable adhesive is a hot melt adhesive such as Findley Adhesive 2031 available from Findley Adhesives of Elmgrove, Wis. Such integration of the topsheet 22 with the absorbent core 26 maintains contact between the topsheet 22 and the core 26 during wear, and provides capillary suction of the fluids passing through the topsheet 22 into the core 26.

The sanitary napkin 20 according to the present invention has the core 26 and the associated topsheet 22 decoupled from the backsheet 24 such that the topsheet 22 is joined to the backsheet 24 to provide independent Z-direction movement of the topsheet 22 and the core 26 relative to the backsheet 24. A suitable sanitary napkin construction for providing such Z-direction decoupled motion of the topsheet 22 and the core 26 relative to the backsheet 24 is disclosed in U.S. Pat. No. 5,007,906 issued Apr. 16, 1991 to Osborn et al., which patent is incorporated herein by reference. Such decoupling is desirable to permit the topsheet 22 and the core 26 to be lifted by the spring 100 into contact with the wearer's body, while allowing the backsheet 24 to remain anchored to the wearer's garment by the attachment means 38.

The sanitary napkin 20 can have a means for controlling the amount of Z-direction separation of the topsheet 22 and the associated core 26 from the backsheet 24. One suitable means for providing such control is one or more longitudinally extending pleats 52 which form a connection joining the topsheet 22 to the backsheet 24. As used herein a "longitudinally extending pleat" is a component of the sanitary napkin 20 having a longitudinally extending fold line 54 to provide one or more Z-direction layers of material along the fold line 54. Preferably two longitudinally extending pleats 52 are provided, one at each longitudinal end 28 of the sanitary napkin 20.

The longitudinally extending pleat 52 may be an extension of the topsheet 22, an extension of the backsheet 24, or a separate piece of material having one end joined to the topsheet 22 and one end joined to the backsheet 24. The portion of the topsheet 22 which forms each pleat is folded under a portion of the topsheet 22 laterally inboard of the longitudinal ends 28 and joined to the backsheet 24 along bond lines 56. Bond lines 56 can comprise heat sealing or adhesive bond lines. Bond lines 56 are preferably continuous to form a seal between the topsheet 22 and the backsheet 24, and can comprise lines of adhesive bonding between the topsheet 22 and the backsheet 24.

Figure 6:
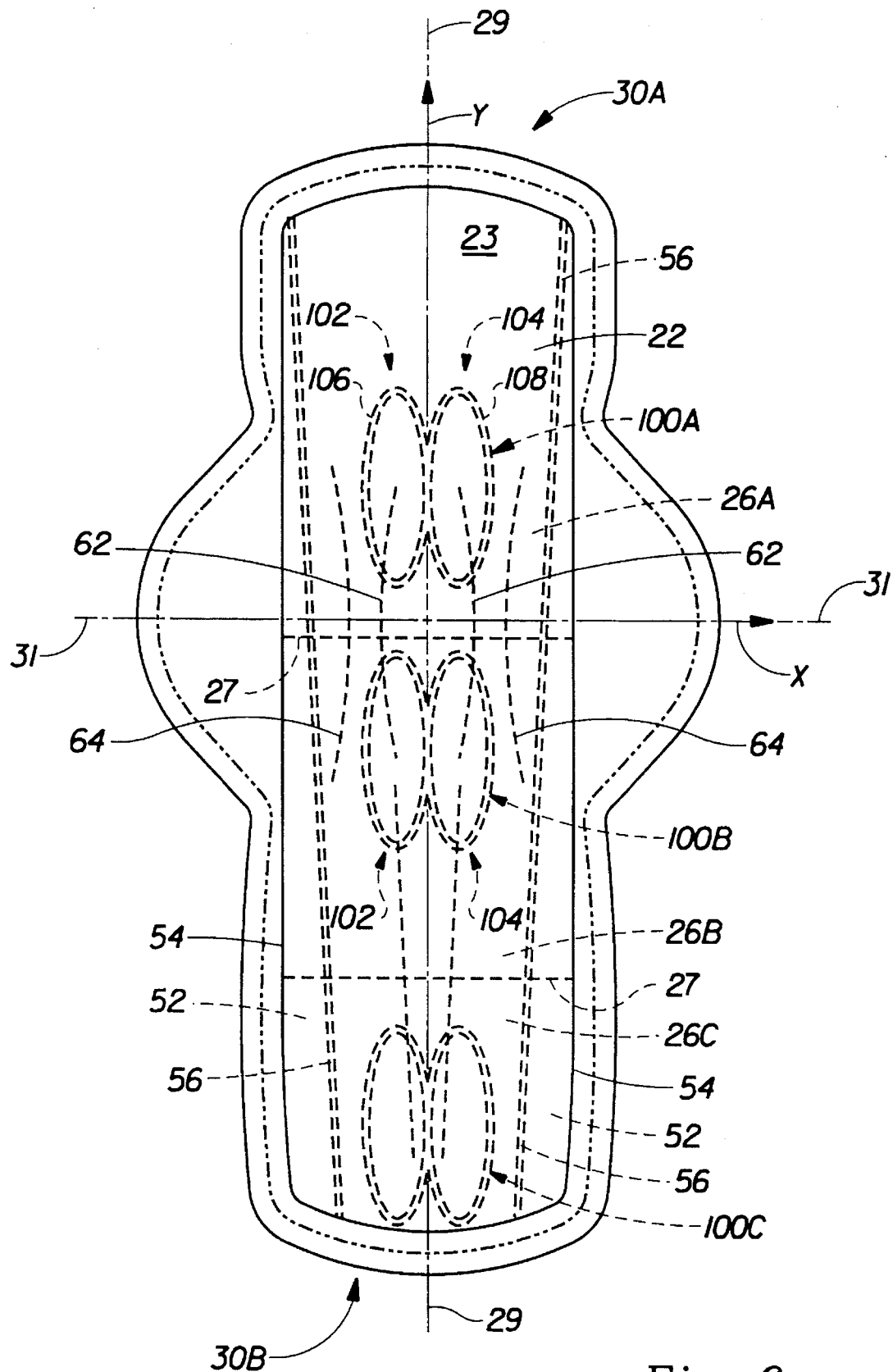
FIG. 6 is a top plan view of a relatively long sanitary napkin of the present invention having a plurality of springs disposed along the longitudinal axis of the sanitary napkin.

The pleats 52 have a lateral width W (FIG. 2) as measured from the bond line 56 to the fold line 54 at a position laterally adjacent a spring 100. The width W can be selected to accommodate a desired amount of Z-direction displacement of the topsheet 22 relative to the backsheet 24 provided by the spring 100. The bond lines 56 and the fold lines 54 can be generally parallel, as shown in FIG. 1, to accommodate a equal amount of Z-direction displacement along the length of the sanitary napkin 20. Alternatively, the bond lines 56 or the fold lines 54 can diverge or converge along the length of the sanitary napkin 20, as shown in FIG. 6, to accommodate different amounts of Z-direction displacement of the topsheet 22 and core 26 along the length of the sanitary napkin 20.

The pleats 52 shown in FIGS. 1-3 are extensions of the topsheet 22 and comprise a single fold line 54 to form a C-shaped pleat. Alternatively, accordion-shaped pleats having a plurality of fold lines 54 can be used. Above referenced U.S. Pat. No. 5,007,906 is incorporated herein by reference for the purpose of describing suitable constructions for longitudinally extending pleats 52.

The topsheet 22 may be left unattached to the backsheet 24 at one or both lateral ends 30 to further accommodate Z-direction decoupling of the topsheet 22 from the backsheet 24. Leaving the topsheet 22 unattached to the backsheet 24 at one of the lateral ends 30 further accommodates Z-direction decoupling of the topsheet 22 and core 26 from the backsheet 24. Additionally, leaving the topsheet 22 unattached to the backsheet at one of the lateral ends 30, such as at a rear lateral end 30B (FIG. 6), also accommodates decoupling of the topsheet 22 and core 26 from the backsheet 24 in the longitudinal direction. Such longitudinal decoupling permits relative movement of the topsheet 22 and core 26 with respect to the backsheet 24 (and the wearer's undergarment to which the backsheet is attached) in the plane of the sanitary napkin 20. The backsheet 24 must take on a radius of curvature different from the radius of curvature of the topsheet 22 and core 26 if the backsheet 24 is to stay attached to the wearer's undergarment while the topsheet 22 and core 26 are in close conformance with the wearer's anatomy. Longitudinal decoupling of the topsheet 22 and core 26 from the backsheet 24, in combination with Z-direction decoupling of the topsheet 22 and core 26 with respect to the backsheet 24, accommodates shear forces caused by this difference in radii of curvature. Additionally, longitudinal segmentation of the core 26, as described below, allows different Z-direction decoupling of the core 26 from the backsheet along the length of the sanitary napkin. Alternatively, longitudinal decoupling can be provided by joining the topsheet 22 to the backsheet 24 at one of the lateral ends 30, such as rear lateral end 30B, by a laterally extending pleat (not shown) to further accommodate Z-direction decoupling and to provide longitudinal decoupling of the topsheet 22 and core 26 with respect to the backsheet 24 in the plane of the sanitary napkin 20.

The combined core 26 and topsheet 22 laminate should be flexible in order that the body facing surface 23 of the topsheet 22 and the second face 42 of the core 26 can be convexly shaped by the spring 100. The laminate of the core 26 and the topsheet 22 can thereby conform to the wearer's body. In a preferred embodiment, the core 26 and the topsheet 22 have a combined Taber bending stiffness, as measured in both the longitudinal and lateral directions, of less than about 3.0 gram-centimeters, and more preferably less than about 2.0 gram-centimeters. The Taber bending stiffness of a sample of the laminate of the topsheet 22 and core 26 with dimensions 3.8 cm (1.5 inch) wide and 3.8 cm (1.5 inch) long can be measured according to TAPPI method T 489 os-76 using a V-5 Stiffness Tester Model 150-B, such as is available from Taber Instruments of the Teledyne Corp., Noah Talawanda, N.Y. The Taber bending stiffness in the longitudinal direction is calculated by averaging at least 10 readings taken from at least 5 samples. Likewise, the Taber stiffness in the lateral direction is calculated using at least 10 readings taken from at least 5 samples. The stiffness test is conducted with a test range of 0–10, a range weight of zero, and a 10 unit compensator weight. The stiffness tester rollers are mounted up to provide a test length of 1.0 cm (0.39 inch). Each sample has a vertically clamped width and is deflected 15 degrees from a centerline position by applying a bending load 1.0 cm (0.39 inch) from the clamps as measured in the longitudinal direction for the longitudinal stiffness value, and as measured in the lateral direction for the lateral stiffness value. Each sample is deflected in two opposite directions using the stiffness tester (e.g., first right, and then left) to provide 2 readings. The average of the readings is divided by the compensator weight (10) to obtain the Taber stiffness value in gram-centimeters.

The laminate of the topsheet 22 and the core 26, or a portion thereof, can be mechanically worked or softened, such as by rolling, to enhance its flexibility. Suitable processes for mechanically working or rolling are described in U.S. Pat. No. 4,107,364 issued to Sisson on Aug. 15, 1978; U.S. Pat. No. 4,834,741 issued to Sabee on May 30, 1989; U.S. Pat. No. 5,143,679 issued Sep. 1, 1992 to Weber et al.; U.S. Pat. No. 5,156,793 issued Oct. 20, 1992 to Buell et al; and U.S. Pat. No. 5,167,897 issued Dec. 1, 1992 to Weber et al., which patents are incorporated herein by reference.

In one embodiment the laminate of the topsheet 22 and the core 26 can comprise at least one pair of longitudinally extending hinge lines symmetrically disposed with respect to the longitudinal axis 29. Referring to FIG. 6, the body facing surface 23 of the topsheet 22 is shown to have a pair of biconvex hinge lines 62 (shown as dotted lines in FIG. 6) positioned laterally inward of a pair of biconcave hinge lines 64. The hinge lines 62, 64 can include, but are not limited to, lines of embossment or compaction, creases, score lines or pre-fold lines. Such longitudinally extending hinge lines 62, 64 facilitate the convex shaping of the body facing surface 23 of the topsheet 22 when the sanitary napkin 20 is in the extended position shown in FIG. 3. The hinge lines 62 help the topsheet 22 and the core 26 to conform to the labia, perianal, or gluteal groove, and the laterally outward hinge lines 64 help the topsheet 22 and the core 26 to conform to the shape of the wearer's legs.

In one embodiment, the ability of the spring 100 to restore the Z-direction caliper of the sanitary napkin 20 is relatively unaffected by wetting of the spring 100. The spring 100 can have a wet caliper reduction which is no more than about 20 percent greater than its dry caliper reduction, and a wet caliper reduction of no more than about eight percent. The wet caliper reduction and dry caliper reduction for the spring 100 are measured using the following procedure repeated for four spring samples.

The spring 100 is adhesively attached to a sheet of polyethylene film having a thickness of about 1.0 mil. The spring 100 and polyethylene film are supported on the horizontal surface of an analytical balance, or other suitable scale. The Z-direction caliper of the spring 100 above the polyethylene film is measured using a suitable displacement measuring system. A suitable displacement measuring system is an "ONO-SOKKI DG" 3610 Digital Gauge and an "ONO-SOKKI GS"-503 Linear Gauge Sensor available from the ONO-SOKKI Corporation of Japan. The Z-direction caliper of the spring 100 is measured at various Z-direction load levels applied to the spring 100 through a circular load application foot having a diameter of 0.95 inch. The load application foot is connected to the linear gauge sensor.

The spring 100 and polyethylene film are placed on the balance, and the balance is tared out to have a zero reading. The initial dry Z-direction caliper of the spring 100 is measured with the load application foot just touching the spring 100, so that the balance indicates a reading of about zero. The Z-direction load on the spring 100 is increased to 32.1 grams in about 5 equal increments, so that the balance indicates a weight of 32.1 grams. The load is then removed, and the unloaded dry Z-direction caliper of the spring 100 is recorded with the load application foot just touching the spring 100, so that the balance indicates a reading of about zero. For each sample, the difference between the initial dry Z-direction caliper and the unloaded dry Z-direction caliper is divided by the initial dry Z-direction caliper to obtain the percentage change in dry caliper of the sample. The dry caliper reduction is the average of the percentage change in dry caliper for the four spring samples.

Each spring (and its associated polyethylene sheet) is completely submerged in distilled water for 10 seconds, and then allowed to drain vertically for 10 seconds. The spring 100 and polyethylene sheet are then supported on the horizontal surface of the analytical balance, and the balanced tared out to indicate a reading of zero. The initial wet Z-direction caliper of the spring 100 is measured with the load application foot just touching the spring 100, so that the balance indicates a reading of about zero. The Z-direction load on the spring 100 is then increased to 32.1 grams in about 5 equal increments. The load is then removed and the unloaded wet Z-direction caliper of the spring 100 is recorded with the load application foot just touching the spring 100, so that the balance indicates a reading of about zero. For each sample, the difference between the initial wet Z-direction caliper and the unloaded wet Z-direction caliper is divided by the initial vet Z-direction caliper to obtain the percentage change in the wet caliper of the sample. The wet caliper reduction of the spring 100 is the average of the percentage change in wet caliper for the four spring samples.

In one embodiment, the spring 100 is nonabsorbent. By "nonabsorbent" it is meant that the spring 100 has an absorbency capacity of less than 100 percent. The absorbency capacity is the ratio of the weight of the water absorbed by a dry sample to the dry sample weight. A nonabsorbent spring 100 is believed to have the advantage that its stiffness and/or its ability to displace the core upward are relatively unaffected by body fluids entering the sanitary napkin 20, as compared to a spring which is absorbent. The absorbency capacity of the spring is measured by first weighing the spring 100 to obtain its dry weight, and then completely submerging the spring 100 in distilled water for 10 seconds. After 10 seconds the spring 100 is removed from the water. The spring is then allowed to drain vertically for 10 seconds. Water adhering to the surface of the spring is then removed by blotting the spring between two pieces of filter paper for 10 seconds. The spring 100 is blotted by placing a first piece of filter paper on a dry horizontal surface, placing the spring on the first piece of filter paper, placing a second piece of filter paper on top of the spring to cover the spring, and placing a piece of 0.25 inch thick Plexiglas weighing 0.26 pound on top of the second piece of filter paper to cover the portion of the second piece of filter paper overlying the spring. A suitable filter paper for blotting the spring 100 is filtration paper having a relatively smooth surface, a particle retention size of greater than about 20–25 micrometers, and a Herzberg filtration speed of about 37 seconds, where the filtration speed is the time for 100 ml of prefiltered water to pass through a 10.0 square centimeter piece of filter paper with a constant head pressure of 10 centimeters of water. A suitable filtration paper is Whatman 4 filtration paper manufactured by Whatman Ltd. of England and available from the Fisher Scientific Company of Pittsburgh, Pa. After blotting the spring 100 for 10 seconds, the spring 100 is immediately weighed to obtain the wet sample weight. The dry weight is subtracted from the wet weight to yield the grams of water absorbed by the dry sample. The percentage absorbency capacity is obtained by dividing the grams of water absorbed by the dry sample weight, and multiplying the quotient by 100.

In a preferred embodiment the spring 100 is hydrophobic. A surface is hydrophobic if the contact angle between a liquid and the surface is greater than 90 degrees. The American Chemical Society Publication "Contact Angle, Wettability, and Adhesion," edited by Robert F. Gould and copyrighted in 1964 is incorporated herein by reference for the purpose of showing how the contact angle can be determined.

In a preferred embodiment the spring 100 comprises a filament spring. By the term "filament spring" it is meant that the spring 100 comprises one or more slender spring sections, each spring section having a length dimension L (FIG. 5) at least 10 times, and preferably at least 100 times its maximum cross-section dimension D. Each spring section can comprise a plastic monofilament construction having a generally round cross-section, such as a nylon monofilament with a diameter D of between about 0.010 inch and about 0.10 inch, and more preferably between about 0.015 inch and about 0.030 inch. A generally round filament cross-section is desirable to eliminate sharp edges which could otherwise cause wearer discomfort, though other cross-sections can be used. Suitable plastic monofilaments are commercially available as 25 lb and 40 lb Berkley "TRILENE XT" manufactured by the Berkley Outdoor Technologies Group of Spirit Lake, Iowa.

Referring to FIGS. 1–5, the filament spring 100 can comprise a three dimensional network when the sanitary napkin 20 is in the extended position shown in FIGS. 3–5. The spring 100 can comprise two legs 102 and 104, which are preferably non-parallel as viewed along the longitudinal axis of the sanitary napkin 20 when the sanitary napkin is in the extended position. The legs 102 and 104 can be joined to the absorbent core 26 at a first position 111 along the longitudinal centerline 29 of the sanitary napkin 20. The legs 102 and 104 can be joined to the backsheet 24 at laterally spaced apart second and third positions 113 and 115, respectively. The legs 102 and 104 can be joined to the absorbent core 26 at the first position 111 and to the backsheet 24 at the second and third positions 113 and 115 by any suitable method, including but not limited to adhesive bonding, mechanical bonding, ultrasonic bonding, and thermal bonding. Suitable adhesives for joining the legs 102 and 104 to the backsheet 24 and to the absorbent core 26 include an adhesive tape available from Anchor Continental, Inc., 3 Sigma Division, of Covington, Ohio, and Century Adhesive A305-IV by the Century Adhesives Corp. of Columbus, Ohio.

Figure 9:
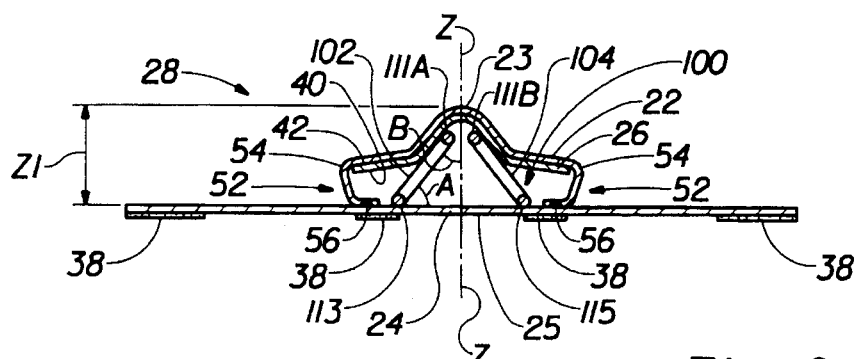
FIG. 9 is a section view of a sanitary napkin showing the sanitary napkin in an extended configuration and having a filament spring comprising two separate legs spaced apart from one another in the lateral direction.

In one embodiment the two legs 102 and 104 are formed from a continuous piece of filament. Alternatively, the legs 102 and 104 can be separate pieces which are spaced apart in the lateral direction. FIG. 9 shows a spring 100 comprising two separate pieces of filament forming two laterally spaced apart legs 102 and 104. The legs 102 and 104 are joined to the core 26 at laterally spaced apart first positions 111A and 111B, respectively, and are joined to the backsheet at second and third positions 113 and 115, respectively.

The second and third positions 113 and 115 are preferably symmetrically positioned with respect to the longitudinal centerline 29 of the sanitary napkin 20. The legs 102 and 104 can thereby form an inverted V shape as viewed along the longitudinal axis 29 when the sanitary napkin is in the extended position shown in FIGS. 3–5. The inverted V shape of the legs 102 and 104 provides a tent frame-like structure which displaces the portions of the topsheet 22 and core 26 along the longitudinal centerline 29 from the backsheet 42, and convexly shapes the body facing surface 23 of the topsheet 22 along the longitudinal centerline 29. The legs 102 and 104 preferably form an included angle A (FIG. 3) of between about 5 degrees and about 85 degrees with a line parallel to the lateral centerline 31 when the sanitary napkin 20 is in the extended position shown in FIGS. 3–5. The legs 102 and 104 preferably form an included angle B (FIGS. 3 and 9) with the Z-axis of less than 90 degrees, and more preferably less than 60 degrees. The tent frame-like structure of the spring 100 is compressible such that the legs 102 and 104 lie substantially in a plane generally perpendicular to the Z-direction under a compressive Z-direction load (e.g. load 200), as shown in FIG. 2, thereby reducing the angle A to about zero degrees.

The inverted V shape of the spring 100 can also provide additional Z-direction displacement of the topsheet 22 and core 26 relative to the backsheet 24 in response to laterally inward directed forces exerted by the wearer's legs. Laterally inward directed forces exerted by the wearer's legs can cause the portion of the legs 102 and 104 joined to the backsheet 24 at the second and third positions 113, 115 to move laterally inward (toward the longitudinal centerline 29) relative to each other. Such laterally inward movement of the legs 102 and 104 causes the inverted V shape of the spring 100 to narrow in the lateral direction, thereby reducing the angle B to about zero degrees. This lateral narrowing of the spring 100 causes the spring 100 to increase the force exerted on the core 26 and topsheet 22 in the Z-direction. The spring 100 can thereby provide further Z-direction displacement of the topsheet 22 and core 26 relative to the backsheet 24 when the spring 100 is compressed laterally. Such laterally inward movement of the legs 102 and 104 also permits the topsheet 22 and core 26 to be compressed to have a relatively thin lateral caliper at relatively low lateral load levels to promote conformance of the topsheet and core with the wearer's body in the labia, perianal, and/or gluteal groove areas.

The leg 102 preferably comprises a first arcuate segment 103 extending between the first position 111 and the second position 113. The leg 104 preferably comprises a second arcuate segment 105 extending between the first position 111 and the third position 115. The arcuate segments 103 and 105 are symmetrically disposed with respect to the longitudinal centerline 29 so that the spring 100 provides restoring forces that are symmetric with respect to the longitudinal centerline 29. The arcuate segments 103 and 105 provide the legs 102 and 104 with flexibility to facilitate the deflection of the spring 100 from the extended position shown in FIG. 3 to the compressed position shown in FIG. 2. The arcuate segments 103 and 105 also provide flexibility in the longitudinal direction, and thereby permit relative longitudinal motion of the topsheet 22 and core 26 relative to the backsheet 24.

The arcuate segments 103 and 105 preferably subtend an angle of at least 90 degrees, and more preferably an angle of at least 180 degrees. In one preferred embodiment each leg 102 comprises one or more closed loops 106 joined to the core 26 and the backsheet 24 at diametrically opposed positions 111 and 113, and each leg 104 comprises one or more closed loops 108 joined to the core 26 and the backsheet 24 at diametrically opposed positions 111 and 115. The closed loops 106 and 108 preferably have a generally circular or oval ring shape.

The Z-direction stiffness and the Z-direction height of the spring 100 can be varied by varying the size of the closed loops 106 and 108, and by varying the lateral spacing of the positions 113 and 115 at which the closed loops 106 and 108 are joined to the backsheet 24. The Z-direction stiffness of the spring 100 will generally decrease as the circumference of the closed loops 106 and 108 is increased. For a given circumference of the loops 106 and 108, the Z-direction stiffness and the Z-direction height of the spring 100 will decrease as the lateral spacing of the positions 113 and 115 is increased. The closed loops 106 and 108 preferably have a circumference of at least 5.1 cm (2.0 inch), and more preferably have a circumference of between about 7.6 cm (3.0 inch) and about 20.3 cm (8.0 inch). The closed loops 106 and 108 are preferably joined to the backsheet 24 at second and third positions 113 and 115, respectively, which are laterally spaced apart a distance of between about 1.0 cm and about 5.0 cm, as measured with the backsheet 24 extended in a generally flat configuration, as shown in FIG. 3. Additionally, the Z-direction stiffness of the spring 100 can also be varied in other ways, such as by varying the dimension D, by varying the material from which the spring 100 is formed, and by providing multiple closed loops 106 and 108 to form the spring legs 102 and 104, respectively. The legs 102 and 104 can overlap in a scissors-like configuration as shown in FIG. 1 and 5 to facilitate deflection of the spring 100 from the extended position shown in FIG. 3 to the compressed position shown in FIG. 2.

The sanitary napkin 20 having a spring 100 with the legs 102 and 104 can be characterized in having a Z-direction stiffness that decreases as the Z-direction caliper is decreased from Z1 in FIG. 3 to Z2 in FIG. 2. The Z-direction stiffness is the change in Z-direction force required to produce a unit Z-direction displacement of the topsheet 22 relative to the backsheet 24. Without being limited by theory, it is believed that the resistance that the legs 102 and 104 provide to Z-direction compression decreases as the angle A (FIG. 3) decreases. Accordingly, the wearer comfort is maintained as the sanitary napkin 20 is compressed from the extended position shown in FIG. 3 to the compressed position shown in FIG. 2. Of course, once the spring 100 is flattened, the Z-direction stiffness of the sanitary napkin 20 will increase with further displacement of the topsheet 22 relative to the backsheet 24.

Referring to FIG. 6, a sanitary napkin 20 having front and rear lateral ends 30A, 30B can have a plurality of springs 100 such as springs 100A, 100B, and 100C positioned along the longitudinal axis 29. The springs 100A–C are shown as dotted lines in FIG. 6 and are arranged from the front to the rear of the sanitary napkin 20 respectively. The spring 100A can provide conformance of the topsheet 22 with the wearer's labial groove, the spring 100B can provide conformance of the topsheet 22 with the wearer's perianal groove, and the spring 100C can provide conformance of the topsheet 22 with the wearer's gluteal groove.

As shown in FIG. 6, the core 26 can be segmented to comprise a plurality of core segments 26A, 26B, and 26C which are independently displaceable in the Z-direction. At least one spring 100 can be associated with each core segment 26A–C to provide independent Z-direction displacement of the core segments 26A–C relative to the backsheet 24. The adjacent core segments, such as core segments 26A, B and 26B, C can be joined by laterally extending hinge lines 27. The hinge lines 27 can include, but are not limited to lines of embossment or compaction, creases, score lines or pre-fold lines. Alternatively, adjacent core segments 26A, B and 26B, C can be unattached, and are indirectly joined to each other by the topsheet 22.

A sanitary napkin 20 comprising the filament spring 100 can have a first Z-direction caliper Z1 at a Z-direction compressive load of 2 grams, and a second Z-direction caliper Z2 at a Z-direction compressive load of less than 100 grams, wherein the second Z-direction caliper is at least 15 millimeters less than the first Z-direction caliper Z1. More preferably, the second Z-direction caliper is at least 15 millimeters less than the first Z-direction caliper at a Z-direction compressive load of less than 50 grams. Even more preferably, the second Z-direction caliper is at least 15 millimeters less than the first Z-direction caliper at a compressive load of less than 25 grams.

A sanitary napkin 20 comprising the filament spring 100 can also have a first Z-direction caliper Z1 at a Z-direction compressive load of 2 grams, and a second Z-direction caliper Z2 at least 25 millimeters less than the first Z-direction caliper Z1 at a Z-direction compressive load of less than 100 grams. More preferably, the second Z-direction caliper is at least 25 millimeters less than the first Z-direction caliper at a Z-direction load of less than 50 grams. The filament spring 100 also provides a sanitary napkin 20 having a Z-direction caliper of less than 10 millimeters, and preferably less than 5 millimeters, under a Z-direction compressive load of 90 grams. The filament spring can thereby promote body conformance and wearer comfort by maintaining the topsheet in contact with the wearer's body, while providing relatively low resistance to compression of the sanitary napkin in the Z-direction.

A sanitary napkin 20 having the filament spring 100 can have a lateral caliper of less than 10 millimeters at a lateral compressive load of 100 grams, more preferably a lateral caliper of less than 5 millimeters at a lateral compressive load of 300 grams, and most preferably a lateral caliper of less than 3 millimeters at a compressive load of 1000 grams. The filament spring thereby permits the a portion of the topsheet and core to be compressed laterally at relatively low lateral load levels, thereby promoting conformance of the topsheet and core with the wearer's body in the labia, perianal, and/or gluteal groove areas while simultaneously maintaining wearer comfort.

Figure 7:
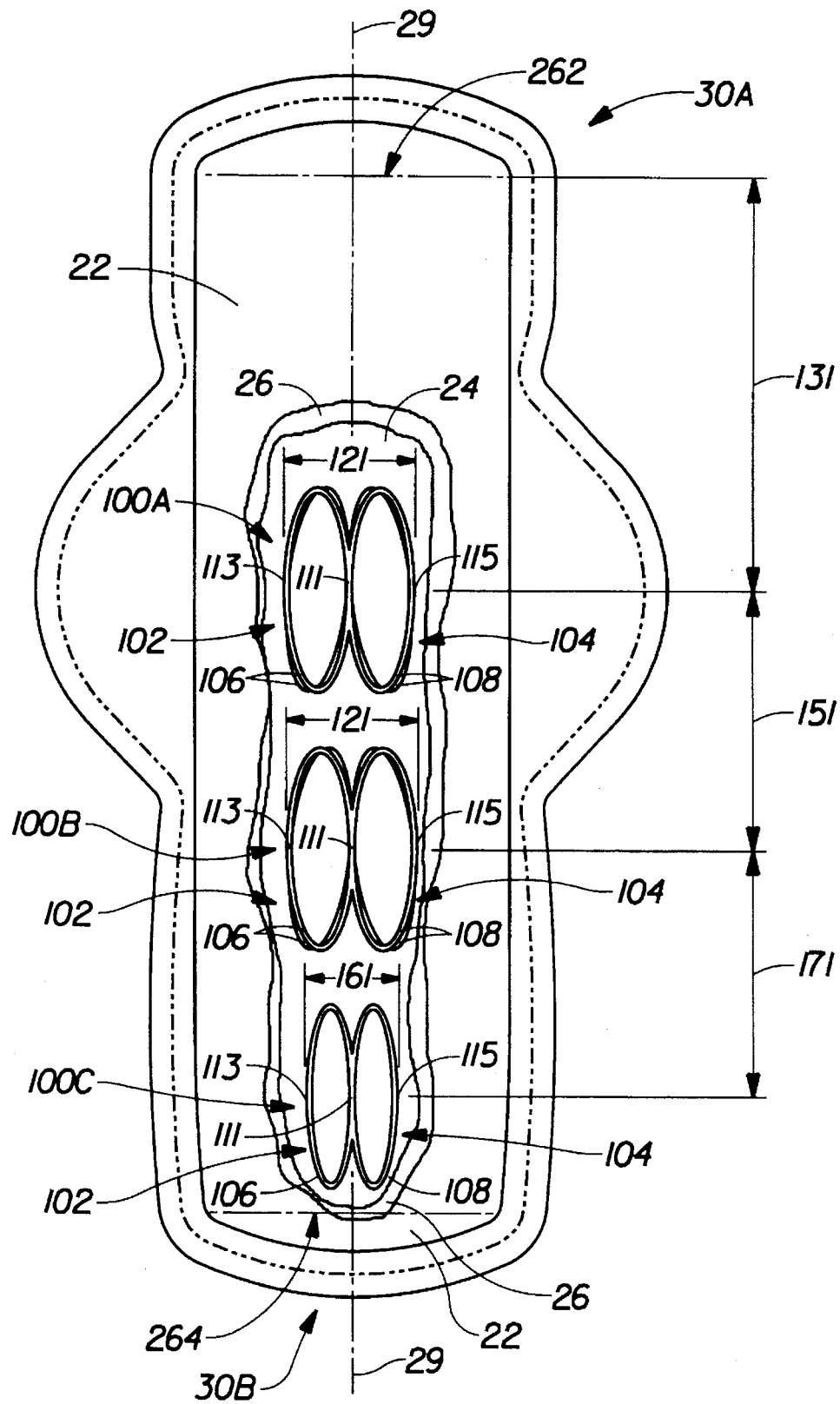
FIG. 7 is a top plan view of a relatively long sanitary napkin of the present invention having springs with different configurations disposed along the longitudinal centerline of the sanitary napkin.

FIG. 7 shows a sanitary napkin 20 having three filament springs, forward spring 100A, middle spring 100B, and rearward spring 100C. A sanitary napkin 20 having the spring configuration shown in FIG. 7 was used to provide the data in Tables 1–4. A description of the filament springs 100A–C and description of the procedure for obtaining the data in Tables 1–4 is provided below.

Referring to FIG. 7, the spring 100A is spaced longitudinally a distance 131 of about 75 mm from a forward lateral end 262 of the absorbent core 26 having a longitudinal length of about 23 cm (forward and lateral ends 262 and 264 are indicated in FIG. 7). The legs 102 and 104 comprise two loops 106 and 108, respectively, of the 25 lb Berkley "TRILENE XT" monofilament. Each of the loops 106 and 108 has a circumference of about 15.2 cm (6.0 inch). The legs 102 and 104 are joined to the backsheet 24 at the second and third positions 113 and 115 laterally spaced apart a distance 121 equal to about 30 mm. The legs 102 and 104 are joined to the core 26 at the first position 111, which is located on the longitudinal centerline 29. The spring 100B has substantially the same construction as the spring 100A, and is spaced longitudinally rearward of the spring 100A a distance 151 equal to about 70 mm.

The spring 100C is spaced longitudinally rearward of the spring 100B a distance 171 equal to about 55 mm. The spring 100C has a leg 102 comprising a single loop 106 of the 25 lb Berkley "TRILENE XT" monofilament. The spring 100C has a leg 104 comprising a single loop 108 of the 25 lb Berkley "TRILENE XT" monofilament. Each of the loops 106 and 108 has a circumference of about 12.7 cm (5.0 inch). The legs 102 and 104 are joined to the backsheet 24 at the second and third positions 113 and 115 laterally spaced apart a distance 161 equal to about 15 mm, and the legs 102 and 104 are joined to the core 26 at the first position 111, which is located on the longitudinal centerline 29.

The Z-direction calipers Z1 and Z2, and the corresponding Z-direction compressive loading listed in Tables 1–3 were measured using the following procedure with an "INSTRON" Model 4502 tensile test machine manufactured by the Instron Engineering Corp. of Canton, Mass. The sanitary napkins 20 to be tested should be conditioned for about 2 hours in a room at between 71 and 75 degree Fahrenheit and 48 to 52 percent relative humidity prior to testing.

The tensile test machine is equipped with a 100 gram load cell. The sanitary napkin 20 is supported, topsheet 22 facing upward, with the garment facing surface 25 of the backsheet 24 facing downward and resting on a horizontal surface of a 6 inch diameter plate attached to the stationary jaw of the tensile test machine. A 1.0 inch diameter horizontal compression foot is attached to the moving crosshead of the tensile test machine to face the topsheet 22 of the sanitary napkin 20. The compression foot is positioned along the longitudinal centerline 29 of the sanitary napkin 20. The data in Table 1 (Front) is measured with the compression foot positioned approximately over the spring 100A, the data in Table 2 (Center) is measured with the compression foot positioned approximately over the spring 100B, and the data in Table 3 (Rear) is measured with the compression foot positioned approximately over the spring 100C.

The initial Z-direction spacing between the stationary plate surface and the compression foot is greater than the unloaded Z-direction caliper of the sanitary napkin 20, and is at least 40 mm. The compression foot is then advanced toward the stationary plate surface at a constant rate (crosshead speed) of 10 inches per minute. The force measured by the load cell for a given spacing between the compression foot and the stationary plate surface is recorded on a strip chart recorder at a chart speed of 20 inches per minute. The spacing between the compression foot and the stationary plate surface at a given load corresponds to the Z-direction caliper of the sanitary napkin 20 at that load. When the spacing between the compression foot and the stationary plate surface has been reduced at least 25 mm from the spacing at a load of 2 grams, or the load measured is greater than 100 grams, the direction of travel of the compression foot is reversed to retract from the stationary plate surface at a speed of 10 inches per minute.

The data in Tables 1–3 were obtained using the above procedure to measure the Z-direction caliper of five sanitary napkins 20.

TABLE 1

FRONT Z-DIRECTION CALIPER AND LOADING

| Measurement | Average | S.D. | Min. | Max. |
|---|---|---|---|---|
| A. Caliper at 2 gm load: | 26.1 mm | 1.47 | 25.0 mm | 28.5 mm |
| B. Caliper at 2 gm unload: | 22.3 mm | 1.64 | 21.0 mm | 25.0 mm |
| C. Caliper reduced 15 mm from A | 11.1 mm | 1.27 | 10.0 mm | 13.5 mm |
| D. Force at Caliper C | 17.9 gm | 3.68 | 14.0 gm | 22.0 gm |
| E. Caliper reduced 25 mm from A | 1.2 mm | | <1 mm | 3.5 mm |
| F. Force at Caliper E | >100 gm | | >100 gm | >100 gm |
| G. Caliper at 90 gm load | 3.3 mm | 0.27 | 3.0 mm | 3.5 mm |

TABLE 2

CENTER Z-DIRECTION CALIPER AND LOADING

| Measurement | Average | S.D. | Min. | Max. |
|---|---|---|---|---|
| A. Caliper at 2 gm load: | 30.2 mm | 1.48 | 28.5 mm | 32 mm |
| B. Caliper at 2 gm unload: | 26.1 mm | 1.56 | 24.5 mm | 28.5 mm |
| C. Caliper reduced 15 mm from A | 15.2 mm | 1.48 | 13.5 mm | 17.0 mm |
| D. Force at Caliper C | 35.1 gm | 7.8 | 23.0 gm | 42.0 gm |
| E. Caliper reduced 25 mm from A | 5.2 mm | 1.48 | 3.5 mm | 7.0 mm |
| F. Force at Caliper E | 38.6 gm | 12.5 | 25.5 gm | 48 gm |
| G. Caliper at 90 gm load | 3.4 mm | 0.55 | 3.0 mm | 4.0 mm |

TABLE 3

REAR Z-DIRECTION CALIPER AND LOADING

| Measurement | Average | S.D. | Min. | Max. |
|---|---|---|---|---|
| A. Caliper at 2 gm load: | 30.7 mm | 1.20 | 29.5 mm | 32 mm |
| B. Caliper at 2 gm unload: | 24.5 mm | 1.80 | 22.0 mm | 26.5 mm |
| C. Caliper reduced 15 mm from A | 15.7 mm | 1.20 | 14.5 mm | 17.0 mm |
| D. Force at Caliper C | 21.9 gm | 2.72 | 18.0 gm | 24.5 gm |
| E. Caliper reduced 25 mm from A | 5.7 mm | 1.20 | 4.5 mm | 7.0 mm |
| F. Force at Caliper E | 33.8 gm | 12.0 | 21 gm | 49.5 gm |
| G. Caliper at 90 gm load | 3.5 mm | 0.35 | 3.0 mm | 4.0 mm |

Tables 1–3 list the average, standard deviation, minimum, and maximum of measurements A–G for five sanitary napkins 20 having the springs 100A–C shown in FIG. 7. Measurement A is the Z-direction caliper of the sanitary napkin 20 at a load cell reading of 2 grams, as the compression foot is advancing toward the stationary plate surface. The caliper at a load of 2 grams is essentially the caliper Z1 of an unloaded sanitary napkin. Measurement B is the Z-direction caliper of the sanitary napkins 20 at a load cell reading of 2 grams, as the compression foot is retracting from the stationary plate surface, and shows that springs 100A–C substantially restore the original, unloaded caliper of the sanitary napkin 20 upon removal of the Z-direction loading.

Measurement C corresponds to a second caliper Z2 which is 15 mm less than the caliper Z1 at 2 grams load, and measurement D is the Z-direction compressive force at the caliper C. Measurement E corresponds to a second caliper Z2 which is 25 mm less than the caliper Z1 at 2 grams load, and measurement F is the Z-direction compressive force measured at the caliper E. Measurement G is the Z-direction caliper of the sanitary napkin 20 when the Z-direction compressive force is equal to 90 grams. In Table 1, the force at caliper E exceeded 100 grams because spring 100A was substantially flattened at that caliper.

Figure 10:
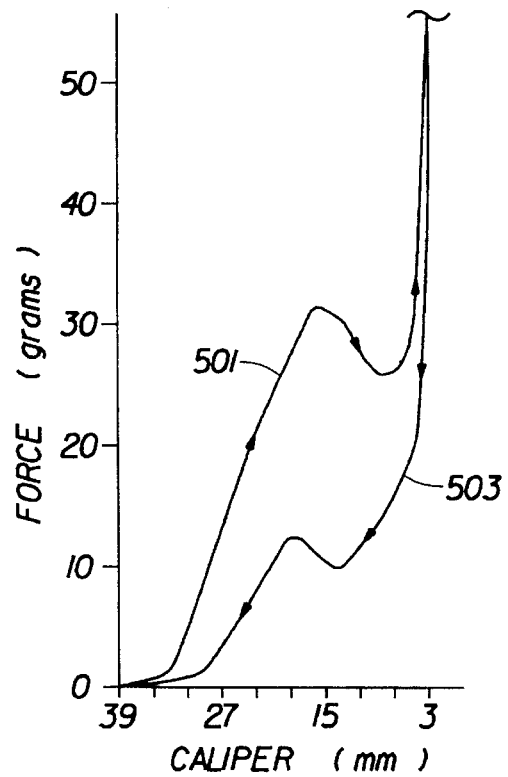
FIG. 10 is a graph of Z-direction force versus Z-direction caliper of a sanitary napkin as shown in FIG. 7, and as measured over spring 100B.

FIG. 10 is a graph showing the Z-direction force measured by the tensile test machine as a function of the Z-direction caliper of a sanitary napkin 20 as shown in FIG. 7, and as measured over the center spring 100B. The portion of graph labeled 501 in FIG. 10 shows the force-caliper relationship as the compression foot was advanced toward the stationary plate surface. The portion of the graph labeled 503 in FIG. 10 shows the force-caliper relationship as the compression foot was retracted from the stationary plate surface. The portion of the graph labeled 501 illustrates that the Z-direction stiffness of the sanitary napkin having a spring 100 can first decrease, and then increase, as the Z-direction caliper of the sanitary napkin is reduced. In particular, the portion of the graph labeled 501 shows that the force first increases to a local maximum as the caliper decreases, decreases to a local minimum as the caliper is further reduced, and then increases as the spring 100B is flattened.

Figure 8:
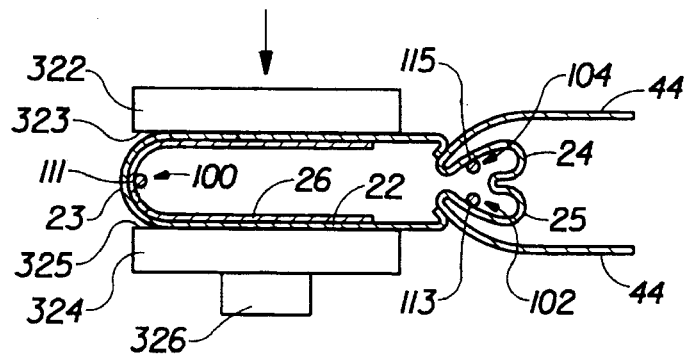
FIG. 8 is a schematic illustration of a cross-section of a sanitary napkin of the present invention disposed between two plates, and showing the method for measuring the lateral caliper of the sanitary napkin under a lateral compressive load.

The sanitary napkin lateral caliper and corresponding lateral load values listed in Table 4 were obtained using the procedure described below, with reference to FIG. 8, and with reference to a sanitary napkin 20 having the springs 100A–C shown in FIG. 7. The sanitary napkins 20 to be tested should be conditioned for about 2 hours in a room at between 71 and 75 degree Fahrenheit and 48 to 52 percent relative humidity prior to testing.

The sanitary napkin 20 is compressed laterally using a constant rate tensile/compression tester such as an "EME" model 599A tester available from EME, Inc. of Newbury, Ohio. The tester should use a load cell with a sensitivity of at least 5 grams and have a load range of at least 2000 grams. The load cell should be calibrated so that force measurements are accurate to within 2 percent for force measurements above 100 grams. The testers measurement of position should be accurate to within at least 0.05 cm. An microcomputer, such as an "IBM" compatible personal computer having an 80386 microprocessor can be used to control the tester and acquire data during testing. The tester and microcomputer can be purchased as a system from EME, Inc.

A first circular plate 322 having a first surface 323 with a diameter of 40 mm is attached to the moving crosshead of the tester. A second circular plate 324 having a second surface 325 with a diameter of 40 mm is attached to the stationary load cell 326 clamp. The plates 322 and 324 are attached to the moving crosshead and the load cell such that the surfaces 323 and 325 are horizontal and parallel.

The surfaces 323 and 325 are initially spaced apart a distance of at least 37.5 mm. The sanitary napkin 20 is partially folded along the longitudinal axis 29 to form a V-shape, with the body facing surface 23 of the topsheet convexly shaped. The sanitary napkin 20 is folded the minimum amount necessary to permit at least a portion of the topsheet 22 and the absorbent core 26 to be positioned between the surfaces 323 and 325. Creasing of the topsheet 22 or the core 26 should be avoided prior to activating the crosshead. The backsheet 24 and the flaps 44 are preferably pulled away from the absorbent core 26 so as not to be positioned between the surfaces 323 and 325. The lateral ends 30 of the sanitary napkin 20 can be held while the sanitary napkin 20 is rested on the surface 325, to prevent the springs 100A–C from causing the sanitary napkin to unfold and fall from between the surfaces 323 and 325. The tester is then started to advance the surface 323 toward the surface 325.

As the surface 323 advances toward the surface 325, the support at the lateral ends 30 can be released. The surface 323 is advanced toward the surface 325 at a constant rate of 0.158 cm/sec. As the surface 323 is advanced toward the surface 325, the topsheet 22 and the core 26 should be folded such that two layers of each of the topsheet 22 and the core 26 are positioned between the surfaces 323 and 325, as shown in FIG. 8, with at least a portion of one of the springs 100 sandwiched between two layers of the core and two layers of the topsheet. Force and displacement values are sampled at a rate of at least 40 data points per second. The lateral caliper of the sanitary napkin (the distance between the surfaces 323 and 325) is recorded at lateral force levels of 50, 100, 300, 1000, and 2000 grams. The lateral caliper and corresponding lateral force measurements are made for at least three sanitary napkins. The average lateral caliper reading for three sanitary napkins is reported at each of the lateral force levels 50, 100, 300, 1000, and 2000 grams in Table 4.

TABLE 4

LATERAL CALIPER AND LOADING

| Measurement | Average | S.D. |
| --- | --- | --- |
| Caliper at 50 gm | 9.3 mm | 0.0 |
| Caliper at 100 gm | 6.1 mm | 0.0 |
| Caliper at 300 gm | 3.8 mm | 0.01 |
| Caliper at 1000 gm | 2.6 mm | 0.01 |
| Caliper at 2000 gm | 1.9 mm | 0.01 |

While particular embodiments of the present invention have been illustrated and described, the scope of the present invention is defined by the appended claims.

What is claimed is:

1. A disposable absorbent article having a longitudinal centerline and longitudinal ends joining first and second lateral ends, the absorbent article comprising:

a liquid pervious topsheet having a body facing surface;

a liquid impervious backsheet joined to the topsheet; and an absorbent core disposed intermediate the topsheet and the backsheet;

the disposable absorbent article having a first Z-direction caliper at a Z-direction compressive load of 2 grams and a second Z-direction caliper at a Z-direction compressive load of less than 100 grams, wherein the second Z-direction caliper is at least 15 millimeters less than the first Z-direction caliper.

2. The disposable absorbent article of claim 1 having a second Z-direction caliper at a Z-direction compressive load of less than 50 grams; wherein the second Z-direction caliper is at least 15 millimeters less than the first Z-direction caliper.

3. The disposable absorbent article of claim 2 having a second Z-direction caliper at a Z-direction compressive load of less than 25 grams; wherein the second Z-direction caliper is at least 15 millimeters less than the first Z-direction caliper.

4. The disposable absorbent article of claim 1 having a lateral caliper of less than 10 millimeters at a lateral compressive load of 100 grams.

5. The disposable absorbent article of claim 1 having a lateral caliper of less than 5 millimeters at a lateral compressive load of 300 grams.

6. The disposable absorbent article of claim 1 having a lateral caliper of less than 3 millimeters at a lateral compressive load of 1000 grams.

7. A disposable absorbent article having a longitudinal centerline and longitudinal edges joining first and second transverse ends, the absorbent article comprising:

a liquid pervious topsheet having a body facing surface;

a liquid impervious backsheet joined to the topsheet; and an absorbent core disposed intermediate the topsheet and the backsheet;

the disposable absorbent article having a first Z-direction caliper at a Z-direction compressive load of 2 grams and a second Z-direction caliper at a Z-direction compressive load of less than 100 grams, wherein the second Z-direction caliper is at least 25 millimeters less than the first Z-direction caliper.

8. The disposable absorbent article of claim 7 having a second Z-direction caliper at a Z-direction compressive load of less than 50 grams; wherein the second Z-direction caliper is at least 25 millimeters less than the first Z-direction caliper.

9. The disposable absorbent article of claim 8 having a Z-direction caliper of less than 10 millimeters at a Z-direction compressive load of 90 grams.

10. The disposable absorbent article of claim 9 having a Z-direction caliper of less than 5 millimeters at a Z-direction compressive load of 90 grams.

\* \* \* \* \*

UNITED STATES PATENT AND TRADEMARK OFFICE
CERTIFICATE OF CORRECTION

PATENT NO. : 5,558,656
DATED : September 24, 1996
INVENTOR(S) : Carl L. Bergman

It is certified that error appears in the above-indentified patent and that said Letters Patent is hereby corrected as shown below:

| | |
|---|---|
| Column 4, line 10 | delete "fiat" and insert --flat--. |
| Column 8, line 19 | delete "Noah" and insert --North--. |
| Column 11, line 37 | delete "tern" and insert --tent--. |

Signed and Sealed this

Third Day of June, 1997

Attest:

BRUCE LEHMAN

Attesting Officer

Commissioner of Patents and Trademarks